United States Patent [19]

Jensen-Korte et al.

[11] Patent Number: 4,908,377

[45] Date of Patent: Mar. 13, 1990

[54] PESTICIDAL SUBSTITUTED 5-ETHYLAMINO-1-ARYLPYRAZOLES

[75] Inventors: Uta Jensen-Korte, Duesseldorf; Otto Schallner, Monheim; Jörg Stetter; Peter Andrews, both of Wuppertal; Benedikt Becker, Mettmann; Bernhard Homeyer, Leverkusen; Wilhelm Stendel, Wuppertal; Wolfgang Behrenz, Overath, all of Fed. Rep. of Germany

[73] Assignee: Bayer Aktiengesellschaft, Leverkusen, Fed. Rep. of Germany

[21] Appl. No.: 201,247

[22] Filed: Jun. 2, 1988

[30] Foreign Application Priority Data

Jun. 12, 1987 [DE] Fed. Rep. of Germany ....... 3719733

[51] Int. Cl.⁴ .................... C07D 231/44; A01N 43/56
[52] U.S. Cl. ..................... 514/404; 548/362; 548/376
[58] Field of Search ........................ 548/362, 375, 376; 514/404, 407

[56] References Cited

U.S. PATENT DOCUMENTS 4,614,533  9/1986  Schallner et al. ....................... 71/92

FOREIGN PATENT DOCUMENTS 0201852  11/1986  European Pat. Off. .
0234119   9/1987  European Pat. Off. .
0235628   9/1987  European Pat. Off. .
0260521   3/1988  European Pat. Off. .

*Primary Examiner*—Richard A. Schwartz
*Assistant Examiner*—Richard A. Sharpe
*Attorney, Agent, or Firm*—Sprung Horn Kramer & Woods

[57] ABSTRACT

Pesticidal 5-ethylamino-1-arylpyrazoles of the formula

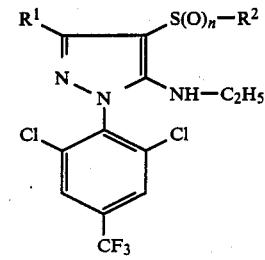

in which
  $R^1$ represents hydrogen or alkyl,
  $R^2$ represents halogenoalkyl and
  n represents a number 0, 1 or 2, with the proviso that if $R^1$ represents hydrogen, $R^2$ is not dichlorofluoromethyl and n is not 0.

These compounds are not only active against plant, hygiene and stored product pests, but also, in the veterinary medicine sector, against animal parasites, such as scaly ticks, argasidae, scab mites, trombidae, flies (stinging and sucking), parasitic fly larvae, lice, hair lice, bird lice and fleas.

9 Claims, No Drawings

PESTICIDAL SUBSTITUTED 5-ETHYLAMINO-1-ARYLPYRAZOLES

The invention relates to new substituted 5-ethylamino-1-arylpyrazoles, several processes for their preparation and their use as pest-combating agents.

It has already been disclosed that certain 5-alkylamino-1-arylpyrazoles such as, for example, 1-(2,6-dichloro-4-trifluoromethyl-phenyl)-5-methylamino-4-trifluoromethylthiopyrazole or 1-(2,6-dichloro-4-trifluoromethylphenyl)-5-methylamino-4-dichlorofluoromethylthiopyrazole possess insecticidal, acaricidal and nematicidal properties (see EP No. 201,852).

However, the activity of these previously known compounds is not completely satisfactory in all areas of application, in particular at low application rates and concentrations.

New substituted 5-ethylamino-1-arylpyrazoles of the general formula (I)

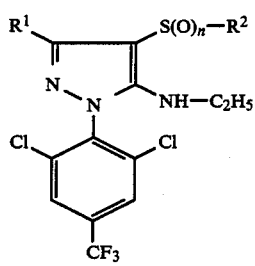   (I)

in which
  $R^1$ represents hydrogen or alkyl,
  $R^2$ represents halogenoalkyl and
  n represents a number 0, 1 or 2, with the exception of the compound of the formula (I) in which $R^1$ represents hydrogen, $R^2$ represents dichlorofluoromethyl and simultaneously n represents 0, have been found.

Furthermore, it has been found that the new substituted 5-ethylamino-1-arylpyrazoles of the general formula (I)

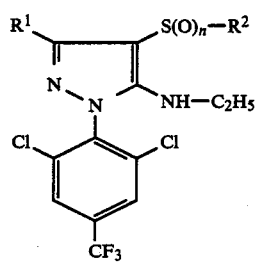   (I)

in which
  $R^1$ represents hydrogen or alkyl,
  $R^2$ represents halogenoalkyl and
  n represents a number 0, 1 or 2, with the exception of the compound of the formula (I) in which $R^1$ represents hydrogen, $R^2$ represents dichlorofluoromethyl and simultaneously n represents 0, are obtained by one of the processes described in the following:

(a) 1-arylpyrazoles of the formula (I)

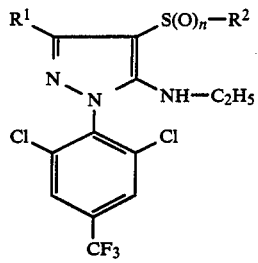   (I)

in which
  $R^1$, $R^2$ and n have the abovementioned meaning, are obtained when 5-amino-1-aryl-pyrazoles of the formula (II)

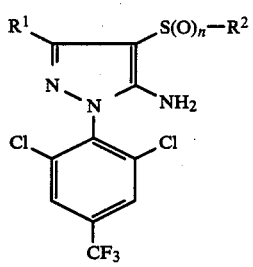   (II)

in which
  $R^1$, $R^2$ and n have the abovementioned meaning, are reacted with alkylating agents of the formula (III)

   (III)

in which
  E represents an electron-attracting leaving group, if desired in the presence of a diluent and if desired in the presence of an acid-binding agent and also if desired in the presence of a catalyst;

(b) substituted 1-arylpyrazoles of the formula (I)

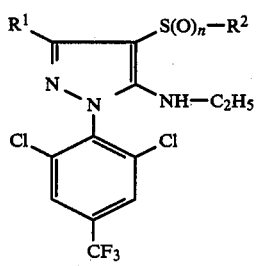   (I)

in which
  $R^1$, $R^2$ and n have the abovementioned meaning, are alternatively also obtained when 5-(N-acylamino)-1-arylpyrazoles of the formula (IV)

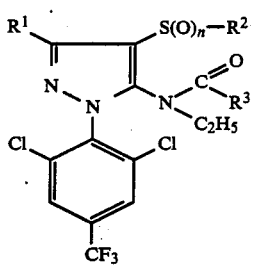

in which

R¹, R² and n have the abovementioned meaning and

R³ represents alkyl, are deacylated with acids as the catalyst if desired in the presence of a diluent;

(c) substituted 1-arylpyrazoles of the formula (Ia)

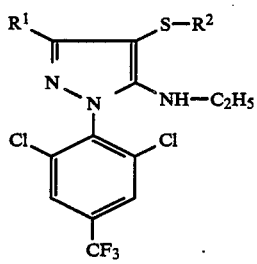

in which

R¹ and R² have the abovementioned meaning, are alternatively also obtained when 4-unsubstituted 1-aryl-pyrazoles of the formula (V)

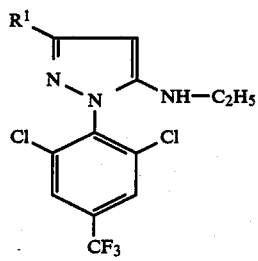

in which

R¹ has the abovementioned meaning, are reacted with sulphenyl halides of the formula (VI)

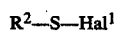

in which

R² has the abovementioned meaning and

Hal¹ represents halogen, if desired in the presence of a diluent and if desired in the presence of an acid-binding agent;

(d) 1-arylpyrazoles of the formula (Ib)

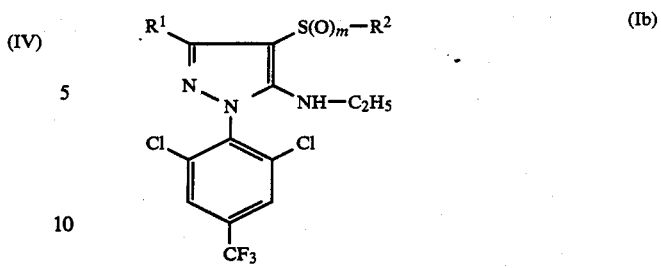

in which

R¹ and R² have the abovementioned meaning and m represents a number 1 or 2, are alternatively also obtained when 1-aryl-pyrazoles of the formula (Ia)

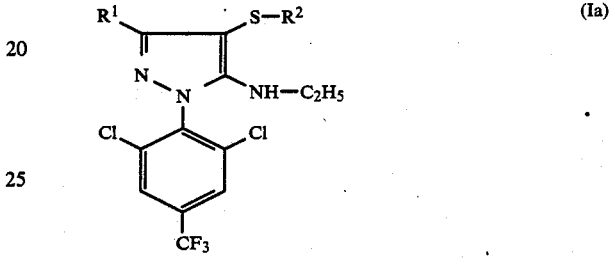

in which

R¹ and R² have the abovementioned meaning, are reacted with an oxidant, if desired in the presence of a diluent and if desired in the presnece of a catalyst and also if desired in the presence of an acid-binding agent;

(e) 1-arylpyrazoles of the formula (Ic)

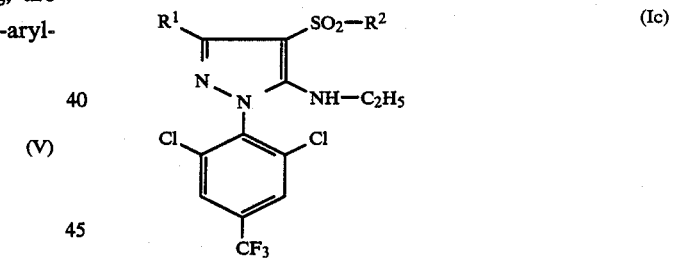

in which

R¹ and R² have the abovementioned meaning, are alternatively also obtained when 5-halogeno-1-aryl-pyrazoles of the formula (VII)

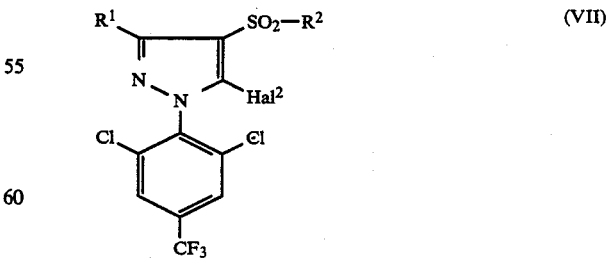

in which

R¹ and R² have the abovementioned meaning and

Hal² represents halogen, are reacted with ethylamine of the formula (VIII)

$C_2H_5-NH_2$ (VIII)

if desired in the presence of a diluent and if desired in the presence of an acid-binding agent.

Finally, it has been found that the new substituted 5-ethylamino-1-arylpyrazoles of the formula (I) possess a very good action against animal pests.

Surprisingly, the substituted 5-ethylamino-1-arylpyrazoles according to the invention show a considerably better action against animal pest than the 1-arylpyrazoles known from the prior art, such as, for example, 1-(2,6-dichloro-4-trifluoromethylphenyl)-5-methylamino-4-dichlorofluoromethylthiopyrazole or 1-(2,6-dichloro-4-trifluoromethylphenyl)-5-methylamino-4-trifluoromethylthio-pyrazole, which are similar compounds chemically and with respect to their action.

Formula (I) provides a general definition of the substituted 5-ethylamino-1-arylpyrazoles according to the invention. Preferred compounds of the formula (I) are those in which $R^1$ represents hydrogen or straight-chain or branched alkyl having 1 to 4 carbon atoms, $R^2$ represents straight-chain or branched halogenoalkyl having 1 to 4 carbon atoms and 1 to 9 identical or different halogen atoms and n represents a number 0, 1 or 2, with the exception of the compound of the formula (I) in which $R^1$ represents hydrogen, $R^2$ represents dichlorofluoromethyl and simultaneously n represents 0.

Particularly preferred compounds of the formula (I) are those in which $R^1$ represents hydrogen, methyl or ethyl, $R^2$ represents chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl or fluorochlorobromomethyl and n represents a number 0, 1 or 2, with the exception of the compound of the formula (I) in which $R^1$ represents hydrogen, $R^2$ represents dichlorofluoromethyl and simultaneously n represents 0.

Very particularly preferred compounds of the formula (I) are those in which $R^1$ represents hydrogen or methyl, $R^2$ represents trifluoromethyl, dichlorofluoromethyl or difluorochloromethyl and n represents a number 0, 1 or 2, with the exception of the compound of the formula (I) in which $R^1$ represents hydrogen, $R^2$ represents dichlorofluoromethyl and simultaneously n represents 0.

If, for example, 5-amino-4-trifluoromethylthio-1-(2,6-dichloro-4-trifluoromethylphenyl)-pyrazole and ethyl iodide are used as starting materials, then the course of the reaction of process (a) according to the invention can be represented by the following equation:

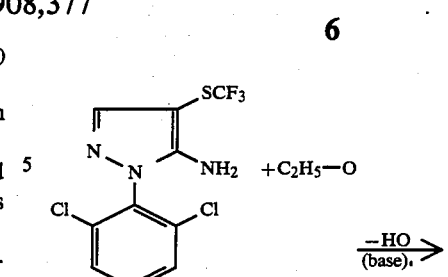

If, the example 3-methyl-4-trifluoromethylthio-5-(N-ethyl-acetamido)-1-(2,6-dichloro-4-trifluoromethylphenyl)-pyrazole is used as the starting compound, then the course of the reaction of process (b) according to the invention can be represented by the following equation:

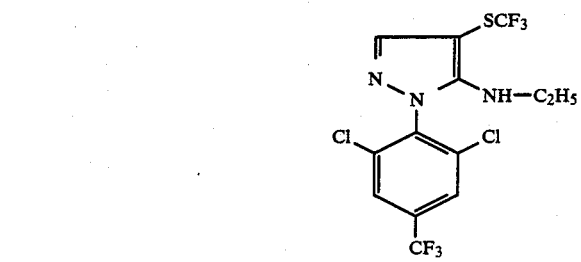

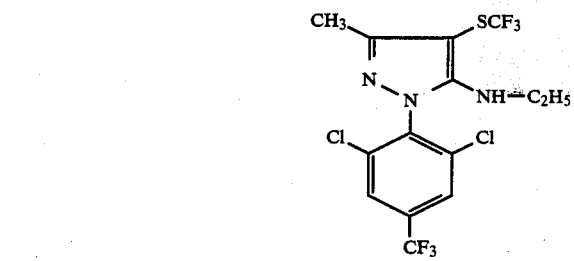

If, for example, 3-methyl-1-(2,6-dichloro-4-trifluoromethylphenyl)-5-ethylamino-pyrazole and trifluoromethanesulphenyl chloride are used as starting materials, then the course of the reaction of process (c) according to the invention can be represented by the following equation:

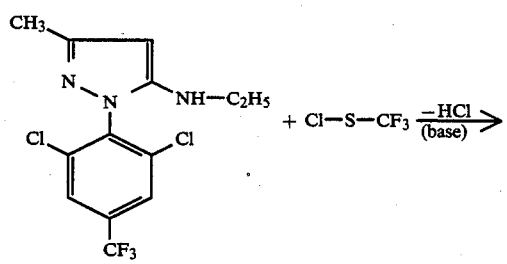

-continued

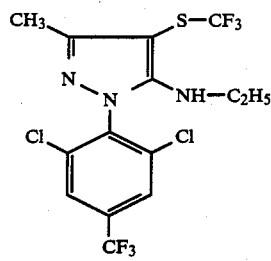

If, for example, 5-ethylamino-4-trifluoromethylthio-1-(2,6-dichloro-4-trifluoromethylphenyl)-pyrazole is used as the starting compound and m-chloroperbenzoic acid as the oxidant, then the course of the reaction of process (d) according to the invention can be represented by the following equation:

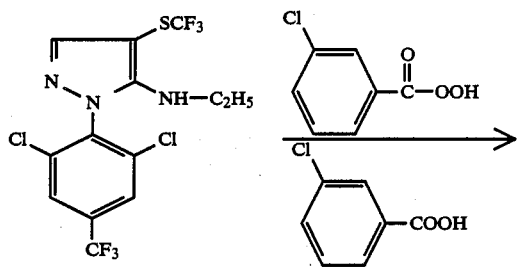

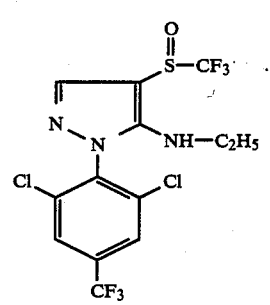

If, for example, 4-dichlorofluoromethylsulphonyl-5-bromo-1-(2,6-dichloro-4-trifluoromethylphenyl)-pyrazole and ethylamine are used as starting materials, then the course of the reaction of process (e) according to the invention can be represented by the following equation:

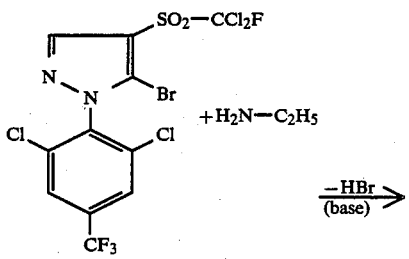

-continued

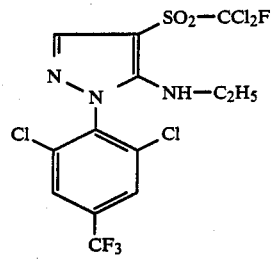

Formula (II) provides a general definition of the 5-amino-1-arylpyrazoles required as starting materials for carrying out process (a) according to the invention. In this formula (II), $R^1$, $R^2$ and n preferably represent those radicals and indices which have already been mentioned as preferred for these substituents and indices in connection with the description of the substances of the formula (I) according to the invention.

The 5-amino-1-aryl-pyrazoles of the formula (II) have been disclosed (see EP No. 201,852).

Formula (III) provides a general definition of the alkylating agents furthermore required as starting materials for carrying out process (a) according to the invention. In this formula (III), E preferably represents halogen, in particular chlorine, bromine or iodine, or ethoxysulphonyloxy or p-toluenesulphonyloxy.

The alkylating agents of the formula (III) are generally known compounds of organic chemistry.

Formula (IV) provides a general definition of the 5-(N-acyl-amino)-1-arylpyrazoles required as starting materials for carrying out process (b) according to the invention. In this formula (IV), $R^1$, $R^2$ and n preferably represent those radicals and indices which have already been mentioned as preferred for these substituents and indices in connection with the description of the substances of the formula (I) according to the invention.

$R^3$ preferabvly represents straight-chain or branched alkyl having 1 to 4 carbon atoms, in particular methyl or ethyl.

The N-acylamino-1-aryl-pyrazoles of the formula (IV) were hitherto unknown. However, they are obtained analogously to known processes (EP No. 201,852) when 5-(N-acylamino)-pyrazoles of the formula (IX)

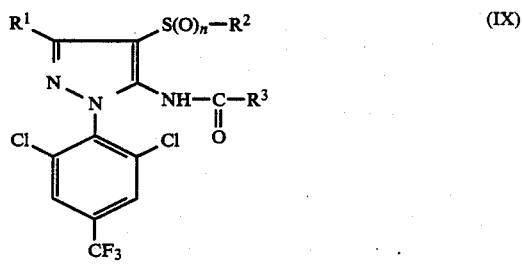

in which
$R^1$, $R^2$, $R^3$ and n have the abovementioned meaning, are reacted with alkylating agents of the formula (III)

$$C_2H_5-E \qquad (III)$$

in which
E represents an electron-attracting leaving group, such as, for example, halogen, in particular chlorine, bromine or iodine, or ethoxysulphonyloxy or p-toluenesulphonyloxy,
analogously to the method of carrying out process (a) according to the invention if desired in the presence of a diluent such as, for example, dichloromethane and if desired in the presence of a base such as, for example, sodium hydroxide solution and also if desired in the presence of a phase transfer catalyst such as, for example, tributylbenzylammonium chloride, at temperatures between 0° C. and 120° C.

The 5-(N-acylamino)-pyrazoles of the formula (IX) have been disclosed (see EP No. 201,852).

Formula (V) provides a general definition of the 4-unsubstituted 1-arylpyrazoles required as starting materials for carrying out process (c) according to the invention. In this formula (V), $R^1$ preferably represents those radicals which have already been mentioned as preferred for this substituent in connection with the description of the substances of the formula (I) according to the invention.

The 4-unsubstituted 1-arylpyrazoles of the formula (V) were hitherto unknown.

However, they are obtained analogously to known processes (see EP No. 201,852) when 5-amino-1-arylpyrazoles of the formula (X)

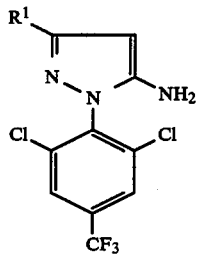 (X)

in which
$R^1$ has the abovementioned meaning, are reacted with alkylating agents of the formula (III)

   $C_2H_5$—E   (III)

in which
E represents an electron-attracting leaving group, such as, for example, halogen, in particular chlorine, bromine or iodine, or ethoxysulphonyloxy or p-toluenesulphonyloxy,
analogously to the method of carrying out process (a) according to the invention if desired in the presence of a diluent such as, for example, dichloromethane, at temperatures between 0° C. and 150° C.; in a reaction variant to this process, it is also possible to prepare the alkylating agent of the formula (III) directly in the reaction vessel from concentrated sulphuric acid and ethanol for the case in which e in formula (III) represents an ethoxysulphonyloxy group and to react it further directly with the 5-amino-1-aryl-pyrazoles of the formula (X) in a single-vessel process (compare also the preparation examples).

The 5-amino-1-aryl-pyrazoles of the formula (X) have been disclosed or are obtainable analoguously to known processes (see EP No. 201,852).

Formula (VI) provides a general definition of the sulphenyl halides additionally required as starting materials for carrying out process (c) according to the invention. In this formula (VI), $R^2$ preferably represents those radicals which have already been mentioned as preferred for this substituent in connection with the description of the substances of the formula (I) according to the invention.

$Hal^1$ preferably represent chlorine.

The sulphenyl halides of the formula (VI) are generally known compounds of organic chemistry.

Formula (Ia) provides a general definition of the 1-arylpyrazoles required as starting materials for carrying out process (d) according to the invention. In this formula (Ia), $R^1$ and $R^2$ preferably represent those radicals which have already been mentioned as preferred for these substituents in connection with the description of the substances of the formula (I) according to the invention.

The 1-arylpyrazoles of the formula (Ia) are compounds according to the invention and are obtainable with the aid of processes (a), (b) or (c) according to the invention.

Formula (VII) provides a general definition of the 5-halogeno-1-arylpyrazoles required as statring materials for carrying out process (e) according to the invention. In this formula (VII), $R^1$ and $R^2$ preferably represent those radicals which have already been mentioned as preferred for these substituents in connection with the description of the substances of the formula (I) according to the invention.

$Hal^2$ preferably represents chlorine or bromine.

The 5-halogeno-1-aryl-pyrazoles of the formula (VII) have been disclosed (see DE-OS (German Published Specification) No. 3,529,829).

Ethylamine, additionally required as a starting compound for carrying out process (e) according to the invention, is a generally known compound of organic chemistry.

Suitable diluents for carrying out process (a) according to the invention are inert organic solvents. These include in particular aliphatic or aromatic, optionally haolgenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or sulphoxides, such as dimethyl sulphoxide.

If desired, process (a) according to the invention can also be carried out in a two-phase system, such as, for example, water/toluene or water/dichloromethane, if desired in the presence of a phase-transfer catalyst. Examples which may be mentioned of such catalysts are: tetrabutylammonium iodide, tetrabutylammonium bromide, tributyl-methylphosphonium bromide, timethyl-$C_{13}$/$C_{15}$-alkylammonium chloride, dibenzyl-dimethylammonium methylsulphate, dimethyl-$C_{12}$/$C_{14}$-alkyl-benzylammonium chloride, tetrabutylammonium hydroxide, 15-crown-5, 18-crown-6, triethylbenzylammonium chloride and trimethylbenzylammonium chloride.

All customarily usable inorganic and organic bases are suitable as acid-binding agents for carrying out process (a) according to the invention. Hydrides, hydorxides, amides, alcoholates, carbonates or hydrogen carbonates of alkali metals, such as, for example, sodium hydride, sodium amide, sodium methylate, sodium hydroxide, sodium carbonate or sodium hydrogen carbonate and also tertiary amines, such as, for example, triethylamine, N,N-dimethylaniline, pyridine, 4-(N,N-dimethylamino)-pyridine, diazabicyclooctane (DABCO), diazabicyclononene (DBN) or diazabicycloundecene (DBU) are preferably used.

The reaction temperatures can be varied within a substantial range when carrying out process (a) according to the invention. In general, the reaction is carried out between −20° C. and +150° C., preferably between 0° C. and +100° C.

For carrying out process (a) according to the invention, 1.0 to 20.0 mol, preferably 1.0 to 15.0 mol, of alkylating agent of the formula (III) and if desired 1.0 to 3.0 mol, preferably 1.0 to 2.0 mol, of acid-binding agent and also 0.01 to 1.0 mol of phase-transfer catalyst are employed per mol of 5-amino-1-aryl-pyrazole of the formula (II). The reaction is carried out, and the reaction products of the formula (I) are worked up and isolated, in a generally customary manner.

Suitable diluents for carrying out process (b) according to the invention are inorganic or organic polar solvents. Alcohols, such as, for example, methanol, ethanol or propanol, or their mixtures with water, are preferably used.

Preferred catalysts for carrying out process (b) according to the invention are inorganic mineral acids, in particular hydrochloric acid or sulphuric acid.

The reaction temperatures can be varied within a substantial range when carrying out process (b) according to the invention. In general, the reaction is carried out between +20° C. and +150° C., preferably between +50° C. and +120° C.

For carrying out process (b) according to the invention, 1.0 to 20.0 mol, preferably 1.0 to 10.0 mol, of acid catalyst are generally employed per mol of 5-(N-acylamino)-1-aryl-pyrazole of the formula (IV) and the mixture is warmed for several hours to the required reaction temperature. The reaction products of the formula (I) are worked up, isolated and purified by customary methods.

Suitable diluents for carrying out process (c) according to the invention are inert organic solvents. These include in particular aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric traimide, esters, such as ethyl acetate, sulphoxides, such as dimethyl sulphoxide or acids such as, for example, acetic acid.

If desired, process (c) according to the invention is carried out in the presence of an acid-binding agent. Those which are suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

The reaction temperatures can be varied within a substantial range when carrying out process (c) according to the invention. In general, the reaction is carried out at temperatures between −20° C. and +120° C., preferably at temperatures between 0° C. and +50° C.

For carrying out process (c) according to the invention, 1.0 to 2.5 mol, preferably 1.0 to 1.5 mol, of sulphenyl halide of the formula (VI) and 1.0 to 2.5 mol, preferably 1.0 to 1.5 mol, of acid-binding agent are generally employed per mol of 4-unsubstituted 1-arylpyrazole of the formula (V). The reaction is carried out, and the reaction products of the formula (Ia) are worked up and isolated, by generally customary processes.

All inorganic or organic oxidants which are customarily suitable for sulphur oxidations can be used as oxidants for carrying out process (d) according to the invention. Organic peracids, such as, for example, peracetic acid, 4-nitroperbenzoic acid or 3-chloroperbenzoic acid, inorganic peracids, such as, for example, periodic acid and also hydrogen peroxide, potassium permanganate or chromic acid are preferably used.

Suitable diluents for carrying out process (d) according to the invention are likewise inert organic solvents. Hydrocarbons, such as benzine, benzene, toluene, hexane or petroleum ether; chlorinated hydrocarbons, such as dichloromethane, 1,2-dichloroethane, chloroform, carbon tetrachloride or chlorobenzene; ethers, such as diethyl ether, dioxane or tetrahydrofuran; carboxylic acids, such as acetic acid or propionic acid, or dipolar aprotic solvents, such as acetonitrile, acetone, ethyl acetate or dimethylformamide are preferably used.

If desired, process (d) according to the invention can be carried out in the presence of an acid-binding agent. Those which are suitable are all customarily usable organic and inorganic acid-binding agents. Hydroxides, acetates or carbonates of alkaline earth metals or alkali metals, such as, for example, calcium hydroxide, sodium hydroxide, sodium acetate or sodium carbonate are preferably used.

If desired, process (d) according to the invention can be carried out in the presence of a suitable catalyst. Those which are suitable are all catalysts which are usually customary for sulphur oxidations of this type. Heavy metal catalysts such as ammonium molybdate may be mentioned by way of example in this connection.

The reaction temperatures can be varied within a substantial range when carrying out process (d) according to the invention. In general, the reaction is carried out at temperatures between −20° C. and +70° C., preferably at temperatures between 0° C. and +50° C.

For carrying out process (d) according to the invention, 0.8 to 1.2 mol, preferably equimolar amounts, of oxidant are generally employed per mol of 1-aryl-pyrazole of the formula (Ia), when it is desired to interrupt the oxidation of the sulphur at the sulphoxide stage. For oxidation to the sulphone, 1.8 to 3.0 mol, preferably two-fold molar amounts of oxidant, are generally employed per mol of 1-aryl-pyrazole of the formula (Ia). The reaction is carried out, and the end products of the formula (Ib) worked up and isolated, by custormay processes.

Suitable diluents for carrying out process (e) according to the invention are inert organic solvents. These include in particular aliphatic, slicyclic or aromatic, optionally halogenated hydrocarbons, such as, for example, benzine, benezne, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or sulphoxides such as dimethyl sulphoxide.

If desired, process (e) according to the invention can be carried out in the presence of a suitable acid-binding agent. Those which are suitable are all customary inorganic or organic bases. These include, for example, alkali metal hydroxides, such as sodium hydroxide or potassium hydroxide, alkali metal carbonates, such as sodium carbonate, potassium carbonate or sodium hydrogen carbonate, and also tertiary amines, such as triethylamine, N,N-diemthylaniline, pyridine, N,N-dimethylaminopyridine, diazabicyclooctane (DABCO), diazabicylclononene (DBN) or diazabicycloundecene (DBU). However, it is also possible to use a suitable excess of ethylamine of the formuola (VIII) employed as a reactant simultaneously as an acid-binding agent.

The reaction temperatures can be varied within a substantial range when carrying out process (e) according to the invention. In general, the reaction is carried out at temperatures between −20° C. and +200° C., preferably at temperatures between 0° C. and +150° C.

For carrying out process (e) according to the invention, 1.0 to 10.0 mol, preferably 1.0 to 5.0 mol, of ethylamine of the formula (VIII) are generally employed per mol of 5-halogeno-1-aryl-pyrazole of the formula (VII). The reaction is carried out, and the reaction products of the formula (Ic) worked up and isolated, by generally customary processes.

The active compounds combine good toleration by plants and favorable homoiotherm toxicity with suitability for combating animal pests, in particular insects and nematodes, which are encounteredc in agriculture, in forestry, in the protection of stored products and of materials, and in the hygiene field. They are active against normally sensitive and resistant species and against all or some stages of development. The above-mentioned pests include:

From the order of the Isopoda, for example, *Oniscus asellus*, *Armadillidium vulgare* and *Porcellio scaber*. From the order of the Diplopoda, for example, *Blaniulus guttulatus*. From the order of the Chilopoda, for example, *Geophilus carpophagus* and *Scutigera spec*. From the order of the Symphyla, for example, *Scutigerella immaculata*. From the order of the Thysanuara, for example, *Lepisma saccharina*. From the order of the Collembola, for example, *Onychiurus armatus*. From the order of the Orthoptera, for example, *Blatta orientalis*, *Periplaneta americana*, *Leucophaea maderae*, *Blattella germanica*, *Acheta domesticus*, *Gryllotalpa spp.*, *Locusta migratoria migratoriodes*, *Melanoplus differentialis* and *Schistocerca gregaria*. From the order of the Dermaptera, for example, *Forficula auricularia*. From the order of the Isoptera, for example, *Reticulitermes spp.*. From the order of the Anoplura, for example, *Phylloxera vastatrix*, *Pemphigus spp.*, *Pediculus humanus corporis*, *Haematopinus spp.* and *Linognathus spp.* From the order of the Mallophaga, for example, *Trichodectes spp.* and *Damalinea spp.* From the order of the Thysanoptera, for example, *Hercinothrips femoralis* and *Thrips tabaci*.

From the order of the Heteroptera, for example, *Eurygaster spp.*, *Dysdercus intermedium*, *Piesma quadrata*, *Cimex lectularius*, *Rhodnius prolixus* and *Triatoma spp*. From the order of the Homoptera, for example, *Aleurodes brassicae*, *Bemisia tabaci*, *Trialeurodes vaporariorum*, *Aphis gossypii*, *Brevicoryne brassicae*, *Cryptomyzus ribis*, *Doralis fabae*, *Doralis pomo*, *Eriosoma lanigerum*, *Hyalopterus arundinis*, *Macrosiphum avenae*, *Myzus spp.*, *Phorodon humuli*, *Rhopalosiphum padi*, *Empoasca spp.*, *Euscelis bilobatus*, *Nephotettix cincticeps*, *Lecanium corni*, *Saissetia oleae*, *Laodelphax striatellus*, *Nilaparvata lugens*, *Aonidiella aurantii*, *Aspidiotus hederae*, *Pseudococcus spp.* and *Psylla spp*. From the order of the Lepidoptera, for example, *Pectinophora gossypiella*, *Bupalus piniarius*, *Chemimatobia brumata*, *Lithocolletis blancardella*, *Hyponomeuta padella*, *Plutella maculipennis*, *Malacosoma neustria*, *Euproctis chrysorrhoea*, *Lymantria spp*. *Bucculatrix thurberiella*, *Phyllocnistis citrella*, *Agrotis spp*. *Euxoa supp.*, *Felthia spp.*, *Earias insulana*, *Heliothis spp.*, *Laphygma exigua*, *Mamestra brassicae*, *Panolis flammea*, *Prodenia litura*, *Spodoptera spp*. *Trichloplusiani*, *Caprocapsa pomonella*, *Pieris spp.*, *Chilo spp.*, *Pyrausta nubilalis*, *Ephestia kuehniella*, *Galleria mellonella*, *Tineola bisselliella*, *Tinea pellionella*, *Hofmannophila pseudospretella*, *Cacoecia podana*, *Capua reticulana*, *Choristoneura fumiferana*, *Clysia ambiguella*, *Homona magnanima* and *Tortrix viridana*. From the order of the Coleoptera, for example, *Anobium punctatum*, *Rhizopertha dominica*, *Bruchidius obtectus*, *Acanthoscelides obtectus*, *Hylotrupes bajulus*, *Agelastica alni*, *Leptionotarsa decemlineata*, *Phaedon cochleariae*, *Diabrotica spp.*, *Psylliodes chrysocephala*, *Epilachna varivestis*, *Atomaria spp*. *Oryzaephilus surinamensis*, *Anthonomus spp*. *Sitophilus spp.*, *Otiorrhynchus sulcatus*, *Cosmopolites sordidus*, *Ceuthorrhynchus assimilis*, *Hypera postica*, *Dermestes spp.*, *Trogoderma spp*. *Anthrenus spp.*, *Attagenus spp*. *Lyctus spp.*, *Meligethes aeneus*, *Ptinus spp.*, *Niptus hololeucus*, *Gibbium psylloides*, *Tribolium spp.*, *Tenebrio molitor*, *Agriotes spp.*, *Conoderus spp.*, *Melolontha melolontha*, *Amphimallon solstitialis* and *Costelytra zealandica*. From the order of the Hymenoptera, for example, *Diprion spp*. *Hoplocampa spp.*, *Lasius spp.*, *Monomorium pharaonis* and *Vespa spp*. From the order of the Diptera, for example, *Aedes spp.*, *Anopheles spp.*, *Culex spp.*, *Drosophila melanogaster*, *Musca spp.*, *Fannia spp.*, *Calliphora erythrocephala*, *Lucilia spp.*, *Chrysomyia spp.*, *Cuterebra spp.*, *Gastrophilus spp.*, *Hyppobosca spp.*, *Stomoxys spp.*, *Oestrus spp.*, *Hypoderma spp.*, *Tabanus spp.*, *Tannia spp.*, *Bibio hortulanus*, *Oscinella frit*, *Phorbia spp.*, *Pegomyia hyoscyami*, *Ceratitis capitata*, *Dacus oleae* and *Tipula paludos*. From the order of the Siphonaptera, for example, *Xenopsylla cheopis* and *Ceratophyllus spp*.

The phytoparasitic nematodes include *Pratylenchus spp.*, *Radophoulus similis*, *Ditylenchus dipsaci*, *Tylenchulus semipenetrans*, *Heterodera spp.*, *Meloidogyne spp.*, *Aphelenchoides spp.*, *Longidorus spp.*, *Xiphinema spp.* and *Trichodorus spp.*.

The active compounds according to the invention are not only active against plant, hygiene and stored product pests, but also, in the veterinary medicine sector, against animal parasites (ectoparasites and endoparasites), such as scaly ticks, argasidae, scab mites, trombidae, flies (stinging and sucking), parasitic fly larvae, lice, hair lice, bird lice and fleas.

They are active against normally sensitive and resistant species and strains, as well as against all parasitic and non-parasitic stages of development of the ectoparasites and endoparasites.

The active compounds of the formula (I) according to the invention are distinguished by a strong insecticidal action. They can be employed particularly against insects which are harmful to plants, such as, for example, against the black bean aphid (Aphis fabae) or against the larvae of the horseradish leaf beetle (Phaedon cocleariae). In this case, the active compounds according to the invention also show leaf systemic properties. In addition, they are outstandingly suitable for combating soil insects and can be employed, for example, for combating Phorbia antiqua grubs or *Diabrotica balteata* larvae in the soil. A noteworthy root systemic action, for example against *Phaedon cochleariae* larvae, can also be emphasized.

In addition, the active compounds according to the invention have a strong action against hygiene pests and stored product pests and can be employed, for example, for combating the common housefly (Musca domestica) or for combating mosquito larvae (Aedes aegypti).

In addition, the active compounds according to the invention can be particularly successfully used for combating pests which live parasitically on warm-blooded animals, such as, for example, against the larvae of the sheep maggot fly (*Lucilia cuprina*) or against cattle ticks (Boophilus microplus) and also against endoparasitic nematodes of the genus *Caenorhabditis elegans*.

The active componds can be converted to the customary formulations, such as solutions, emulsions, suspensions, powders, foams, pastes, granules, aerosols, natural and synthetic materials impregnated with active compound, very fine capsules in polymeric substances and in coating composition for seed, and in formulations used with burning equipment, such as fumigating cartridges, fumigating cans, fumigating coils and the like, as well as ULV cold mist and warm mist formulations.

These formulations are produced in known manner, for example by mixing the actiive compounds with extenders, that is, liquid solvents, liquefied gases under pressure, and/or solid carriers, optionally with the use of surfaceactive agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobuty ketone or cyclohexanone, strongly polar solvents, such as dimethylformamide and dimethyl sulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as finely divided silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkyl sulphates, arylsulphonates as well as albumin hydrolyzation products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use dyestuffs such as inorganic pigments, for example iron oxide, titanium oxide and Prusian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commerically available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and stored product pests, the active compounds are distinguished by an excellent residual reaction on wood and clay as well as a good stability to alkali on limed substrates.

The active compounds which can be used according to the invention are also suitable for combating insects, midges, ticks etc. in the sectors of animal keeping and cattle breeding, where better results, for example higher milk production, greater weight, more attractive animal pelt, longer life etc., can be achieved by combating the pests.

The application of the active compounds which can be used according to the invention occurs in this sector in a known fashion, such as by oral application in the form of, for example, tablets, capsules, potions, granules, by means of dermal or external application in the form of, for example, dipping, spraying, pouring-on, spotting-on and dusting, as well as by means of parenteral application in the form of, for example, injection, and, furthermore, by means of the feed-through process. In addition, application as molded articles (neckband, ear tag) is also possible.

The biological effectiveness of the compounds according to the invention will be explained with reference to the examples below.

PREPARATION EXAMPLES

EXAMPLE 1

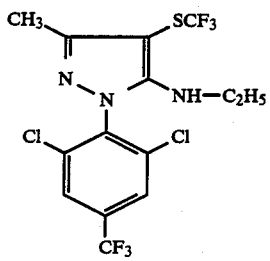
(Process c)

4.2 g (0.033 mol) of trifluoromethanesulphenyl chloride are introduced at 15° C. to 20° C. into a solution of 10.1 g (0.03 mol) of 5-ethylamino-3-methyl-1-(2,6-dichloro-4-trifluoromethylphyenyl)-pyrazole in 50 ml of glacial acetic acid, the mixture is stirred for 6 hours at room temperature, poured into 1 l of ice water and stirred for a further hour, and the deposited precipitate is filtered off with suction, washed neutral with water and dried.

10.4 g (79% of theory) of 5-ethylamino-3-methyl-4-trifluoromethylthio-1-(2,6-dichloro-4-trifluoromethylphenyl)-pyrazole of melting point 53° C.-54° C. are obtained.

PREPARATION OF THE STARTING COMPOUND

EXAMPLE V-1

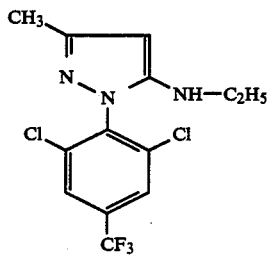

15 ml (11.9 g; 0.26 mol) of ethanol are added dropwise at room temperature to 15.5 g (0.05 mol) of 5-amino-3-methyl-1-(2,6-dichloro-4-trifluoromethylphenyl)-pyrazole (see EP No. 201,852) in 30 ml of concentrated sulphuric acid, the reaction mixture is stirred for 2 hours at 110° C. after completion of the addition (until the starting product is no longer detectable on the thin layer chromatogram), added to 300 ml of ice water and extracted twice with 100 ml of hexane in each case, the aqueous phase is adjusted to pH 7 with sodium hydroxide solution and stirred for 20 hours at room temperature, and the crystalline precipitate is filtered off with suction, washed with water and dried.

11 g (65% of theory) of 5-ethylamino-3-methyl-1-(2,6-dichloro-4-trifluoromethylphenyl)-pyrazole of melting point 74° C.-75° C. are obtained.

EXAMPLE 2

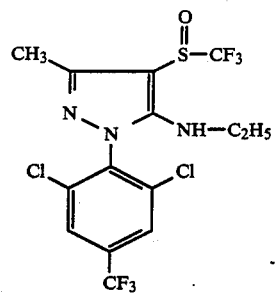
(Process d)

0.7 g (0.007 mol) of a 35 per cent strength aqueous hydrogen peroxide solution are added at room temperature to 3 g (0.007 mol) of 5-ethylamino-3-methyl-4-trifluoromethylthio-1-(2,6-dichloro-4-trifluoromethylphenyl)-pyrazole in 30 ml of sulphuric acid, the mixture is then stirred for 20 hours at room temperatiure, poured into ice water and extracted repeatedly with dichloromethane, and the combined organic phases are dried over magnesium sulphate and the solvent removed in vacuo.

1.6 g (50% of theory) of 5-ethylamino-3-methyl-4-trifluoromethylsulphinyl-1-(2,6-dichloro-4-trifluoromethylphenyl)-pyrazole of melting point 76° C. are obtained.

The following 1-arylpyrazoles of the general formula (I)

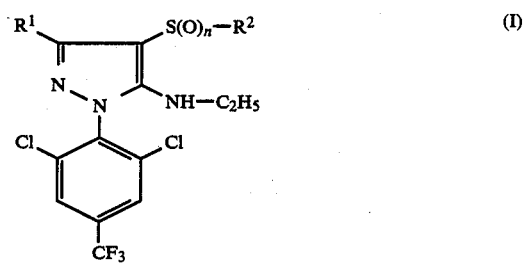

are obtained in a corresponding manner and according to the general instructions for preparation:

| Ex. No. | $R^1$ | $R^2$ | n | melting point /°C. |
|---|---|---|---|---|
| 3 | CH$_3$ | —CCl$_2$F | 0 | 77–81 |
| 4 | CH$_3$ | —CF$_3$ | 2 | 107–108 |
| 5 | CH$_3$ | —CCl$_2$F | 1 | 63–65 |
| 6 | CH$_3$ | —CCl$_2$F | 2 | 160–162 |
| 7 | H | —CF$_3$ | 0 | 57–58 |
| 8 | H | —CCl$_2$F | 1 | 53–58 |
| 9 | H | —CCl$_2$F | 2 | 99–102 |
| 10 | H | —CF$_3$ | 1 | 119–121 |
| 11 | H | —CF$_3$ | 2 | 75–78 |

USE EXAMPLES

The compounds shown below were employed as comparison substances in the following use examples:

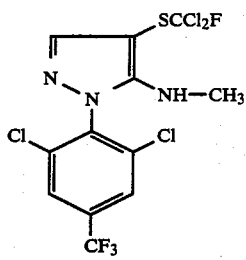

1-(2,6-Dichloro-4-trifluoromethylphenyl)-5-methylamino-4-dichlorofluoromethylthio-pyrazole

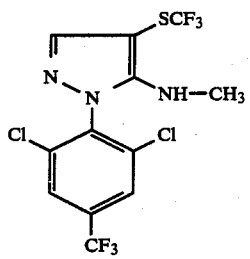

1(2,6-Dichloro-4-trifluoromethylphenyl)-5-methylamino-4-trifluoromethylthio-pyrazole
1-(2,6-Dichloro-4-trifluoromethylphenyl)-5-ethylamino-4-difluoromethylthio-pyrazole

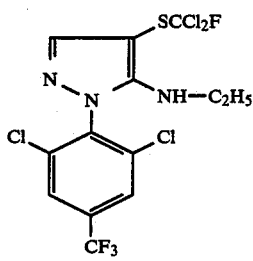

(all known from EP 201,852)

EXAMPLE A

Mosquito Larvae test
Test animals: 4th larval stage *Aedes aegypti*
Solvent: 99 parts by weight of acetone
Emulsifier: 1 part by weight of benzylhydroxydiphenyl polyglycol ether To produce a suitable preparation of active compound, 2 parts by weight of active compound are dissolved in 1,000 parts by volume of solvent, containing the amount of emulsifier stated above. The solution thus obtained is diluted with water to the desired lower concentrations.

The aqueous preparations of active compound of the desired concentration are filled into plastic beakers and 25 mosquito larvae are then placed in each beaker. The larvae are fed daily with fish food (Tetramin ®).

After 24 hours, the degree of destruction in % is determined. 100% means that all larvae have been killed. 0% means that no larvae at all have been killed.

In this test, for example, the following compounds from the preparation examples show superior action compared to the prior art: 1, 2, 3, 4, 7, 9 and 11.

EXAMPLE B $LT_{100}$ test for Diptera
Test animals: *Musca domestica*, resistant
Number of test animals: 25
Solvent: Acetone 2 parts by weight of active compound are taken up in 1,000 parts by volume of solvent. The solution thus obtained is diluted with further solvent to the desired lower concentrations.

2.5 ml of the active compound solution are pipetted into a Petri dish. A filterpaper of about 9.5 cm diameter is located on the bottom of the Petri dish. The Petri dish is left standing open until the solvent has completely evaporated. The amount of active compound per $m^2$ of filterpaper varies, depending on the concentration of the active compound solution. The stated number of test animals is then introduced into the Pedri dish, and the dish is covered with a glass lid.

The condition of the test animals is checked continuously. The time required for a 100% knock-down effect is determined.

In this test, for example, the following compounds from the preparation examples show superior action compared to the prior art: 1, 2, 4, 7, 10, 11.

EXAMPLE C

Phaedon larvae test
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (Brassica oleracea) are treated be being dipped into the preparation of the active compound of the desired concentration and are infested with horseradish leaf better larvae (Phaedon cochleariae), as long as the leaves are still moist.

After the specified periods of time, the destruction in % is determined. 100% means that all the beetle larvae have been killed; 0% means that none of the beetle larvae have been killed.

In this test, for example, the following compounds from the preparation examples show superior action compared to the prior art: 1, 4, 8, 9.

EXAMPLE D

Aphis test (systemic action)
Solvent: 7 parts by weight of dimethylformamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Bean plants (Vicia faba), which are heavily infested by the black bean aphid (Aphis fabae), are watered with 20 ml in each case of active compound preparation of the desired concentration, so that the active compound preparation penetrates into the soil without wetting the shoots. The active compound is taken up by the roots and transported into the shoots.

After the specified periods of time, the destruction in % is determined. 100% means that all the aphids have been killed; 0% means that none of the aphids have been killed.

In this test, for example, the following compounds from the preparation examples show superior action compared to the prior art: 1, 2, 7, 9, 10, 11.

EXAMPLE E

Critical concentration test/root-systemic action
Test insect: *Phaedon cochleariae* larvae
Solvent: 3 parts by weight of acetone
Emulsifierd 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount be weight of active compound per unit volume of soil, which is given in ppm (=mg/l), being decisive. The treated soil is filled into pots and these are planted with cabbage (Brassica oleracea). The active compound can in this way be taken up from the soil by the roots of the plants and be transported into the leaves.

To demonstrate the root-systemic effect, exclusively the leaves are infested with the abovementioned test animals after 7 days. After a further 2 days, the evaluation is made by counting or estimating the dead animals. The root-systemic action of the active compound is deduced from the mortality figures. It is 100% if all test animals have been killed and 0% if just as many test insects are still alive as in the case of the untreated control.

In this test, for example, the following compounds from the preparation examples show superior action compared to the prior art: 1, 2, 7, 9, 11.

EXAMPLE F

Critical concentration test/soil insects
Test insect: *Phorbia antiqua* maggots (in the soil)
Solvent: 3 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show superior action compared to the prior art: 1, 2, 4, 8.

EXAMPLE G

Critical concentration test/soil insects
Test insect: *Diabrotical balteata* larvae (in the soil)
Solvent: 3 parts by weight of acetone
Emulsifer: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance here, only the amount by weight of active compound per unit volume of soil, which is given in ppm (=mg/l), being decisive. The soil is filled into pots and the pots are left to stand at room temperature.

After 24 hours, the test animals are introduced into the treated soil, and after a further 2 to 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, for example, the following compounds from the preparation examples show superior action compared to the prior art: 1, 4.

EXAMPLE H

Test with *Lucilia cuprina* resistant larvae
Emulsifier: 35 parts by weight of ethylene glycol monomethyl ether
35 parts by weight of nonylphenol polyglycol ether To produce a suitable preparation of active compound, three parts by weight of active compound are mixed with seven parts by weight of the abovementioned mixture and the concentrate thus obtained is diluted with water to the particular desired concentration.

About 20 Lucilia cuprina res. larvae are introduced into a test tube with contains approx. 1 cm$^3$ of horse muscle and 0.5 ml of the preparation of active compound. After 24 hours, the degree of destruction is determined.

In this test, for example, the following compounds from the preparation examples show superior action compared to the prior art: 7, 8, 9, 10, 11.

EXAMPLE I

Test with *Boophilus microplus* resistant
Solvent: 35 parts by weight of ethylene glycol monomethyl ether
35 parts by weight of nonylphenol polyglycol ether To produce a suitable preparation of active compound, three parts by weight of active compound are mixed with seven parts by weight of the solvent mixture indicated above, and the condcentrate thus obtained is diluted with water to the desired concentration.

10 adult Boophilus microplus res. are immersed for 1 minute in the active compound preparation to be tested. After transfer to plastic beakers and storage in a climatically controlled chamber, the degree of destruction is determined.

In this test, for example, the following compounds from the preparation examples show superior action compared to the prior art: 1, 2.

EXAMPLE J

In vitro nematode test

*Caenorhabditis elegans*

$10^{-4}$ g of active compound are dissolved in 1 ml of water or 0.1 ml of dimethyl sulphoxide (DMSO). This solution is added to a replica plate. To this is added 2 ml of an E.coli suspension to which 10-20 female animals or larvae of Caenorhabditis elegans in 0.5 ml of sterile M9 buffer solution have been added. The E.coli suspension is prepared by adding 1.8 l of sterile M9 buffer solution to 300 ml of an overnight culture of a Uracil-requiring E.coli strain.

The test sample is incubated for 7 days at 22° C. and then evaluated. The extent to which the active compound influences multiplication is estimated and the concentration at which multiplication is inhibited is given.

In this test, for example, the following compounds from the preparation examples show at least 95% inhibition of the multiplication of the nematode C. elegans at a concentration of $\leq 100$ µg/ml: 2 and 3;

at a concentration of $\leq 10$ µg/ml: 1, 4, 7, 9 and 11.

What is claimed is:

1. A substituted 5-ethylamino-1-arylpyrazole of the formula

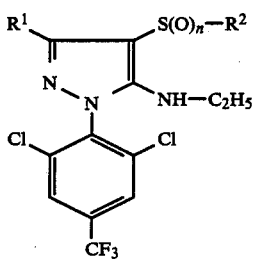

in which $R^1$ represents hydrogen or alkyl, $R^2$ represents halogenoalkyl and n represents a number 0, 1 or 2, with the proviso that if $R^1$ is hydrogen, $R^2$ cannot be dichlorofluoromethyl and n is not 0.

2. A 5-ethylamino-1-arylpyrazole according to claim 1, which $R^1$ represents hydrogen or alkyl having 1 to 4 carbon atoms, $R^2$ represents halogenoalkyl having 1 to 4 carbon atoms and 1 to 9 identical or different halogen atoms and n represents a number 0, 1 or 2, with the proviso that if $R^1$ is hydrogen, $R^2$ cannot be dichlorofluoromethyl and n is not O.

3. A substituted 5-ethylamino-1-arylpyrazole according to claim 1, in which $R^1$ represents hydrogen, methyl or ethyl, $R^2$ represents chloromethyl, difluoromethyl, difluorochloromethyl, fluorodichloromethyl, trifluoromethyl, pentafluoroethyl, pentachloroethyl, fluorotetrachloroethyl, difluorotrichloroethyl, trifluorodichloroethyl, tetrafluorochloroethyl, heptafluoropropyl, chloroethyl, bromoethyl, chloropropyl, bromopropyl, dichloromethyl, chlorofluoromethyl, trichloromethyl, trifluoroethyl, trifluorochloroethyl, tetrafluoroethyl, difluorochloroethyl, fluorodibromomethyl, difluorobromomethyl or fluorochlorobromomethyl and n represents a number 0, 1, or 2, with the proviso that if $R^1$ is hydrogen, $R^2$ cannot be dichlorofluoromethyl and n is not O.

4. A substituted 5-ethylamino-1-arylpyrazole according to claim 1, in which $R^1$ represents hydrogen or methyl, $R^2$ represents trifluoromethyl, dichlorofluoromethyl or difluorochloromethyl and n represents a number 0, 1 or 2, with the proviso that if $R^1$ is hydrogen, $R^2$ cannot be dichlorofluoromethyl and n is not O.

5. A pesticidal composition useful for combating animal pests comprising a pesticidally effective amount of at least one substituted 5-ethylamino-1-aryl-pyrazole according to claim 1 and an extender or carrier therefor.

6. A method of combating animal pests comprising applying to said pests and/or the environment thereof an effective amount of a substituted 5-ethylamino-1-arylpyrazole according to claim 1.

7. A pesticidal composition according to claim 5 wherein the pests are insects or nematodes.

8. A method according to claim 6, wherein the pests are insects or nematodes.

9. A 5-ethylamino-1-arylpyrazole of the formula

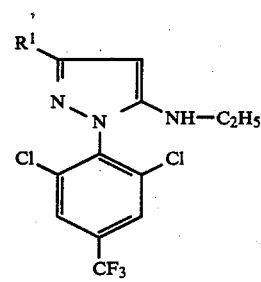

in which $R^1$ represents hydrogen or alkyl.

* * * * *